United States Patent [19]

Frank et al.

[11] Patent Number: 4,935,512
[45] Date of Patent: Jun. 19, 1990

[54] PROCESS FOR THE PREPARATION OF QUINOLINE-CARBOXYLIC ACID DERIVATIVES

[75] Inventors: Judit Frank; Klára Béres née Pálmai; Gábor Kulcsár, all of Budapest, Hungary

[73] Assignee: Chinoin Gyogyszer Es Vegyeszeti Termekek Gyara Rt, Budapest, Hungary

[21] Appl. No.: 273,853

[22] PCT Filed: Oct. 14, 1987

[86] PCT No.: PCT/HU87/00044
§ 371 Date: Jun. 3, 1988
§ 102(e) Date: Jun. 3, 1988

[87] PCT Pub. No.: WO88/02748
PCT Pub. Date: Apr. 21, 1988

[30] Foreign Application Priority Data

Oct. 15, 1986 [HU] Hungary .................. 4292/86
Oct. 1, 1987 [HU] Hungary .................. 4292/86

[51] Int. Cl.$^5$ ........................... C07D 401/04
[52] U.S. Cl. ................................... 544/363
[58] Field of Search .............................. 544/363

[56] References Cited

U.S. PATENT DOCUMENTS 4,292,317 9/1981 Pesson .................. 544/363
4,352,803 10/1982 Matsumoto et al. ........ 544/363
4,599,334 7/1986 Petersen et al. .......... 544/363

Primary Examiner—Richard L. Raymond
Assistant Examiner—James H. Turnipseed
Attorney, Agent, or Firm—Herbert Dubno; Jonathan Myers

[57] ABSTRACT

The invention relates to a new and simple process for the preparation of quinoline-carboxylic acid derivatives of the general formula (I)

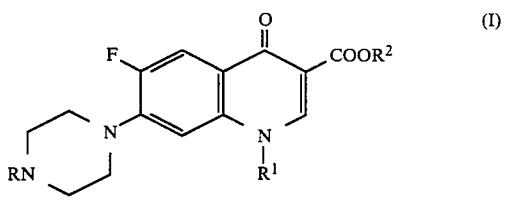

as well as hydrates and therapeutically acceptable salts thereof. In the formula the meaning of the substituents is as follows:

R is hydrogen atom or a formyl group, $R^1$ is a hydrogen atom or a straight or branched chain alkyl group having 1 to 4 carbon atoms, which may be substituted by a hydroxyl group, a halogen atom or an amino group; or a $CH_3$—NH-group, $R^2$ is a hydrogen atom or an alkyl group having 1 to 4 carbon atoms.

According to the invention the compound of the general formula (II)

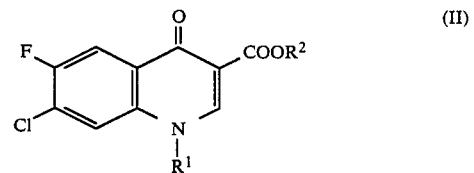

or an acid addition salt thereof is reacted with piperazine in dimethylformamide and—if desired—the compound of the general formula (III)

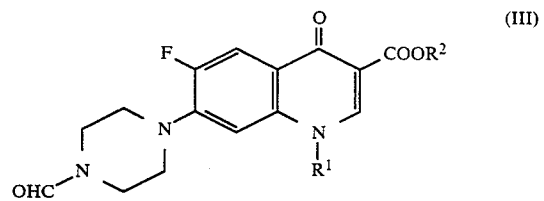

thus obtained is subjected to an acidic or alkaline treatment, or is reacted advantageously with hydrazine or preferably with hydrazine-hydrate.

6 Claims, No Drawings

PROCESS FOR THE PREPARATION OF QUINOLINE-CARBOXYLIC ACID DERIVATIVES

The invention relates to a new and simple process for the preparation of quinoline-carboxylic acid derivatives as well as hydrates and therapeutically acceptable salts thereof. In the formulae the meaning of the substituents is as follows:

R is a hydrogen atom or a formyl group, $R_1$ is a hydrogen atom or a straight or branched chain alkyl group having 1 to 4 carbon atoms, which may be subtituted by a hydroxyl group, a halogen atom or an amino group; or a $CH_3$—NH— group, $R^2$ is a hydrogen atom or an alkyl group having 1 to 4 carbon atoms.

The preparation of compounds of the formula (III)

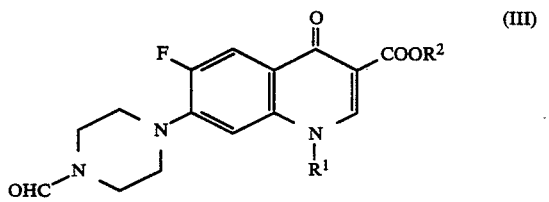

was carried out up to the present by reacting a quinoline-carboxylic acid derivative of the formula

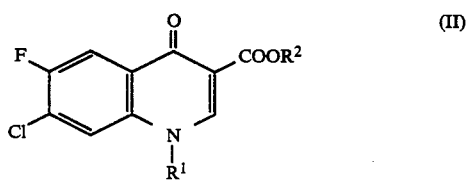

and formyl-piperazine in dimethyl sulfoxide as solvent (Belgine patent specification No. 870576.) Further a process is known to form the free formyl derivative by formylation with formic acid in a yield of 50% (J. Med. Chem. 23 1358, 1980). This latter process is very corrosive because of the application of formic acid.

The disadvantage of these processes is that they are carried out in several steps and in expensive solvents as pyridine, dimethyl sulfoxide, etc. The yields are very low too.

The present invention relates to a process for the preparation of quinoline-carboxylic acids of the formula (I) the hydrates and salts thereof from compounds of the formula (II) in a way, that the compound of the formula (II) or an acid addition salt thereof is reacted with piperazine in dimethylformamide and—if desired—the compound of the formula (III) thus obtained is subjected to an acidic or alkaline treatment, or is reacted advantageously with hydrazine or preferably with hydrazine-hydrate.

Among the compounds of the formula (I)

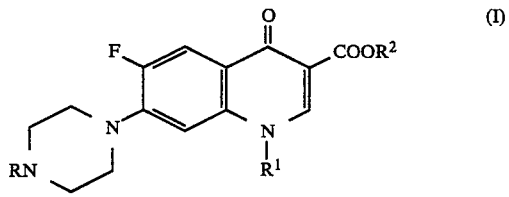

the 1-ethyl-6-fluoro-7-(4-formyl)-piperazinyl-1,4-dihydro-4-oxo-quinoline-3-carboxylic acid possesses a very significant antibacterial effect. It is effective against Pasteurella multocida in an inhibitioning concentration of 0.25 µg/ml, against different Bacillus strains (e.g. Bac. subtilis, Bac. licheniform) in a minimal inhibitioning concentration of 0.5–0.75 g/ml and similarly in a minimal inhibitioning concentration of 0.75 µg/ml against Shigella sonnei and Salmonella cholerae-suis strains, too.

According to the present invention the formylation should be carried out advantageously by heating.

Higher temperature (120°–153° C.) results in a shorter reaction time. The yield of the reaction can be increased by assuring an acidic medium, the reaction time can be decreased respectively. The acidic medium can be assured in a way, that the acid addition salt of the compound of the formula (II) is applied, or advantageously the reaction should be carried out in the presence of an acid, advantageously in the presence of hydrochloric or sulphuric acid.

The processing of the reaction mixture, the recovery of the product occurs in a very simple way. The dimethylformamide applied as solvent and a reagent is removed under reduced pressure and it may be used repeatedly. To the residue water is added and the precipitate is recovered by filtration.

Among the compounds of the formula (I), those of the formula (IV)

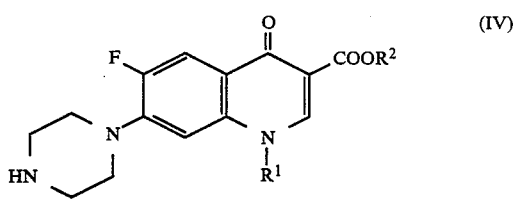

possess valuable antibacterial activities, too (e.g. Antimicrob. Agents Chemother. 1985 581–586). These can be prepared from compounds of the general formula (III) containing the formyl group by acidic or alkaline treatment, or advantageously with hydrazine, preferably with hydrazine-hydrate, optionally in the presence of an acid (e.g. acetic acid).

As acids, first mineral acids, e.g. hydrochloric acid, sulphuric acid, phosphoric acid, etc. are applied in a suitable dilution. As alkali the hydroxides and carbonates of the alkali and alkali earth metals are applied. The removal of the formyl group is carried out in an organic solvent and/or in water. advantageously in an alcohol-water mixture. The most advantageous was a 3:1 mixture of isopropyl alcohol and water. The reaction is carried out at a temperature of 25°–100° C., advantageously at the boiling point higher temperature results in a decreased reaction time.

The product can be obtained advantageously after the neutralization of the acid or alkali excess of the reaction mixture by filtration. If desired the product can be purified by recrystallization. The compounds of the formula (I) can be prepared in the form of hydrates, or the hydrates can be formed they can be set free from their salts respectively, or their therapeutically accepable salts can be formed.

A significant moment of the present process is the recognition, that from the compound of the formula (III) the formyl group can be removed by reacting with hydrazine. This way we succeeded to a realize a new type process, which leads to a more uniform and pure product compared to the hydrolysis processes.

Further details of the present process are shown in the example, without limiting the application to the examples.

EXAMPLE 1

5.4 g (0.02 moles) of 1-ethyl-6-fluoro-7-chloro-1,4-dihydro-4-oxo-quinoline-3-carboxylic acid and 10.4 g (0.12 moles) of piperazine in 120 ml of dimethylforrmamide are heated for 6 hours at 145° C. Thereafter the solvent is removed under reduced pressure and 300 ml of water are added to the residue. The precipitate is obtained by filtration. Thus 4.6 g of 1-ethyl-6-fluoro-7-(4-formyl)-piperazinyl-1,4-dihydro-4-oxo-quinoline-3-carbocyclic acid are obtained, melting at 270° C. After recrystallisation from dimethylformamide the melting point raised to 285°–286° C.

EXAMPLE 2

1.0 g (0.0029 moles) of 1-ethyl-6-fluoro-7-(4-formyl)-piperazinyl-1,4-dihydro-4-oxo-quinoline-3-carboxylic acid is suspended in 40 ml of a 3:1 mixture of isopropyl alcohol and water and 10 ml of 1N hydrochloric acid are added. The reaction mixture is boiled for 5 hours. After cooling the product crystallizes in the form of a hydrochloric acid salt and can be removed by filtration, or after neutralization with a 1N sodium hydroxide solution the precipitated product is filtered. After drying 0.58 g of 1-ethyl-6-fluoro-7-piperazinyl-1,4-dihydro-4-oxo-quionoline-3-carboxylic acid are obtained, melting point 222° C.

EXAMPLE 3

1.0 g (0.0029 moles) of 1-ethyl-6-fluoro-7-(4-formyl)-piperazinyl-1,4-dihydro-4-oxo-quinoline-3-carboxylic acid is suspended in 40 ml of a 3:1 mixture of isopropyl alcohol and water and 5 ml of an aqueous 1N sodium hydroxide solution are added. The reaction mixture is boiled for 8 hours. After cooling the solution is neutralized with a diluted hydrochloric acid solution. The precipitated product is filtered. The resulting 0.6 of 1-ethyl-6-fluoro-7-piperazinyl-1,4-dihydro-4-oxo-quinoline-3-carboxylic acid melts at 218° C.

EXAMPLE 4

1.0 g (0.0029 moles) of 1-ethyl-6-fluoro-7-(4-formyl)-piperazinyl-1,4-dihydro-4-oxo-quinoline-3-carboxylic acid is suspended in 50 ml of a 3:1 mixture of isopropyl alcohol and water and 0.5 ml (0.010 moles) of a 98% hydrazine-hydrate and 0.6 ml (0.010 moles) of acetic acid are added. The reaction mixture is heated at 100° C. for 6 hours. The product crystallizing from the cooled solution is obtained by filtration. Thus 0.827 g of the 1-ethyl-6-fluoro-7-piperazinyl-1,4-dihydro-4-oxo-quinoline-3-carboxylic acid melting at 222° C. are obtained.

EXAMPLE 5

1.35 g (0.005 moles) of 1-ethyl-6fluoro-7-chloro-1,4-dihydro-4-oxo-quinoline-3-carboxylic acid, 2.6 g (0.03 moles) of piperazine and 1 ml of a concentrated hydrochloric acid are heated at boiling temperature in 30 ml of dimethylformamide for 4 hours. The solvent is removed under reduced pressure and to the residue 80 ml of water are added. The precipitated product is filtered and washed with water. After drying 1.42 g (82%) of 1-ethyl-6-fluoro-7-(4-formyl)-piperazinyl-1,4-dihydro-4-oxo-quinoline-3-carboxylic acid are obtained melting at 288° C.

We claim:

1. A process for the preparation of a compound of the Formula (I)

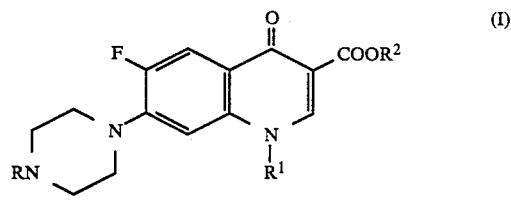

or a hydrate or a pharmaceutically acceptable salt thereof wherein

R is hydrogen or formyl;

$R^1$ is hydrogen, $C_1$ to $C_4$ straight or branched chain alkyl unsubstituted or substituted by halogen, hydroxy or amino, or methylamino; and $R^2$ is hydrogen or lower alkyl; which comprises the steps of:

(a) aminating a compound of the Formula (II)

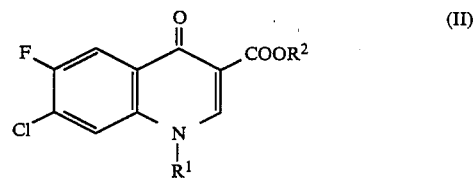

with piperazine in dimethylformamide, said dimethylformamide serving as both a solvent and as sole formylating reagent to N-formylate the 4-position of the piperazine, to produce the compound of the Formula (I) where R is formyl; and in the case wherein the compound of the Formula (I) includes R as hydrogen; and (b) treating the compound of the Formula (I) where R is formyl with an acid or with an alkali or with hydrazine or hydrazine hydrate to yield the desired product.

2. The process defined in claim 1 wherein according to step (a) the amination of the compund of the Formula (II) with piperazine and dimethylformamide is carried out in an acidic medium.

3. The process defined in claim 1 wherein according to step (b) the compound of the Formula (I) where R is formyl is treated with a mineral acid or an alkali.

4. The process defined in claim 1 wherein according to step (b) the hydrazinic, acidic or alkaline treatment of the compound of the Formula (I) where R is formyl is carried out in a mixture of isopropanol and water.

5. The process defined in claim 1 wherein according to step (b) the treatment of the compound of the Formula (I) where R is formyl is carried out with hydrazine or hydrazine hydrate to yield the compound of the Formula (I) where R is hydrogen.

6. A process for the preparation of a compound of the Formula (IV)

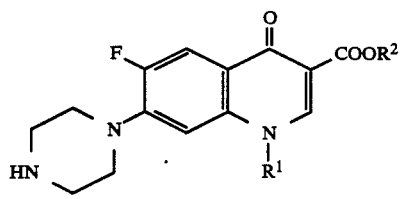 (IV)

or a hydrate or a pharmaceutically acceptable salt thereof wherein $R^1$ is hydrogen, $C^1$ to $C^4$ straight or branched chain alkayl unsubstituted or substituted by halogen, hydroxy or amino; or methylamino; and $R^2$ is hydrogen or lower alkyl; which comprises the steps of:

(a) aminating a compound of the Formula (II)

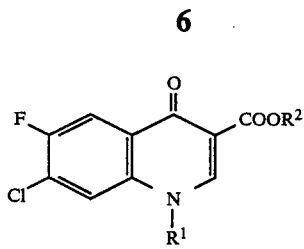 (II)

with piperazine in dimethylformamide, said dimethylformamide serving as both a solvent and as sole formylating reagent to N-formylate the 4-position of the piperazine, to produce the compound of the Formula (III)

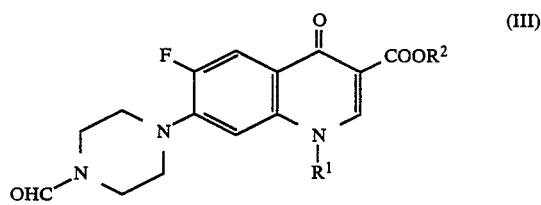 (III)

and (b) treating the compound of the Formula (III) with hydrazine or hydrazine hydrate to yield the desired compound.

* * * * *